US00PP21316P3

(12) United States Plant Patent
Sheehan

(10) Patent No.: US PP21,316 P3
(45) Date of Patent: Sep. 28, 2010

(54) GRAPEVINE PLANT NAMED 'SHEEGENE-3'

(50) Latin Name: *Vitis vinifera*
Varietal Denomination: Sheegene-3

(76) Inventor: Timothy P. Sheehan, 120 Olivewood Ct., Porterville, CA (US) 93257

( * ) Notice: Subject to any disclaimer, the term of this patent is extended or adjusted under 35 U.S.C. 154(b) by 566 days.

(21) Appl. No.: 11/594,528

(22) Filed: Nov. 8, 2006

(65) Prior Publication Data

US 2008/0134383 P1 Jun. 5, 2008

(51) Int. Cl.
*A01H 5/00* (2006.01)

(52) U.S. Cl. ..... Plt./205

(58) Field of Classification Search ..... Plt./205
See application file for complete search history.

(56) References Cited

U.S. PATENT DOCUMENTS

PP4,787 P * 11/1981 Olmo et al. ..... Plt./205
PP17,504 P3 * 3/2007 Maranto ..... Plt./207

* cited by examiner

*Primary Examiner*—Wendy C. Haas
(74) *Attorney, Agent, or Firm*—Baker Manock & Jensen, PC; Eric C. Cole, Esq.

(57) ABSTRACT

The new and distinct variety characterized by a very large red seedless grape that ripens in early August three weeks later than the 'Flame Seedless' Grape (unpatented) with good favor, juicy and firm skin. The berries are born on strong woody stems and branches and are well adapted to commercial handling.

1 Drawing Sheet

Latin name of the genius and species of the plant claimed: *Vitis vinifera.*

Variety denomination: 'SHEEGENE-3'.

The claimed plant relates to a new and distinct variety of *Vitis vinifera* to be known as 'Sheegene-3'. The new variety of *Vitis vinifera* is the result of hybridization of 'Princess' (unpatented), the pollen parent, and 'Red Globe' (U.S. Plant Pat. No. 4,787), the seed parent. The new variety was first hybridized in the late spring of 2000 by Timothy P. Sheehan of Porterville, Calif., producing a medium to large red seedless grape in early August. The new variety was asexually propagated in the dormant season of 2003/2004 by Timothy P. Sheehan, grafted on 'Harmony' (unpatented) virus-free grape rootstock on six vines. The new variety was planted in a *Vitis vinifera* variety block near Fowler, Calif. on the west side of Thompson Road, north of Adams Road. The red-colored grapes produced by the new variety are medium to large in size with very good flavor and have been shown to maintain their distinguishing characteristics throughout asexual propagation.

BACKGROUND OF THE INVENTION

The present invention relates to a new and distinct variety of grape which will hereafter be denominated as 'Sheegene-3' and more particularly as a grapevine that produces a red seedless table grape which matures in early August in the San Joaquin Valley of Central California. The present variety produces a grape that resembles the 'Flame Seedless' Grape (unpatented) but differs because it is larger and has a sweeter flavor than the 'Flame Seedless' Grape (unpatented) and matures about three weeks later.

SUMMARY OF THE INVENTION

The claimed plant is characterized by producing a medium to large red seedless grape with very good flavor that is mature for harvesting and shipment in early August. The new variety of grape was propagated in the San Joaquin valley of Central California, and it can be compared to the 'Flame Seedless' Grape (unpatented) but that it matures three weeks later, among other distinguishing characteristics.

BRIEF DESCRIPTION OF THE DRAWING

The colored photograph has across the top on the left secondary growth cluster; in the middle is a shoot growth with small leaves followed by another secondary growth cluster on the right; in the middle on the left is a mature cluster with a leaf and petiole displaying the upper leaf surface. Right below in the middle are 4 berries cut in half (2 longitudinal and 2 horizontal) displaying the color of the flesh. Across the bottom is a leaf and petiole with the lower side of the leaf displayed; to the right is a small shoot with tendrils; at the bottom is mature cane with leaves and nodes.

DETAILED BOTANICAL DESCRIPTION

Referring more particularly to horticultural details of the new and distinct variety of grapevine, the following description has been observed under the ecological conditions prevailing at the origin vineyard that is located east of Fowler, Calif, in the San Joaquin valley of Central California.

All major color descriptions are by reference to the Dictionary of Color by Maerz and Paul, First Edition, published in 1930. Common colors names are also used in several instances.

Vine:

*Size.*—Medium to large for a four year old vine.

*Vigor.*—Very good.

*Chilling requirements.*—Normal for grapevine in the San Joaquin Valley of Central California.

*Figure.*—With wide cordons forming a "T" shape figure.

*Production capacity.*—Very good.
*Regularity of bearing.*—Regular.

Trunk:
*Size.*—Medium to large — 8½ inch circumference (21.59 cm) 27 inches above graft.
*Surface texture.*—Rough, shaggy.
*Color of bark.*—P1.7 J9 Tanagra Castilian Brown, Old Cedar.
*Mature canes—color.*—P1.7 J7 Roan.
*Nodes.*—Five.
*Length between nodes.*—7.62 to 11.4 cm (3 to 4½ inches)
*Lenticels—number.*—None.
*Lenticels—size.*—0.
*Shoots—contour.*—Droops.
*Tendrils—number.*—One at node.
*Tendrils—length.*—4 to 8.3 cm (1.57 to 3.27 inches).
*Tendrils—form.*—Bifurcate.
*Tendrils—texture.*—Firm to woody.
*Buds—shape.*—Triangular.
*Buds—size.*—6 to 7 mm in width (0.24 to 0.28 inches); 7 to 8 mm in length (0.28 to 0.31 inches).
*Buds fruitfulness.*—Very Good.

Branches:
*Size.*—Medium to large (15.24 cm circumference).
*Surface texture.*—Slightly rough.
*Color—one year old wood.*—P1.7 E9 Kaffa Hamstead Brown.
*Color—immature branches.*—P1.22 L7 —Art gr.
*Surface texture.*—Immature branches — smooth.

Leaves:
*Size.*—Medium to large.
*Density.*—Dense.
*Average length.*—10.6 to 13 cm. (4.17 to 5.12 inches).
*Average width.*—6.69 to 7.09 cm (17 to 18 inches).
*Shape.*—Pentagonal.
*Texture—upper surface.*—Smooth.
*Texture—lower surface.*—Glabrous.
*Color—upward disposed surface.*—P1.23 J9 — polo green.
*Color—downward disposed surface.*—P1.21 17 Fern green.
*Color—leaf vein.*—P1.18 L6 Love Bird.
*Marginal form.*—Generally slightly undulate.
*Leaf vein thickness.*—2 mm (0.079 inch).
*Leaf margin.*—Toothed.
*Glandular characteristics.*—0.
*Petiole—size.*—Large.
*Petiole—length.*—12 to 14 cm (4.72 to 5.52 inches).
*Petiole—thickness.*—2 mm (0.079 inches).
*Petiole—color.*—P1.7 L5 close to Viridine gr.
*Petiole—sinus form.*—Reverse "U" shape.
*Stem glands.*—None observed.
*Lobe average.*—Four.
*Tooth—size.*—8 mm (0.31 inches} in width; 10 mm (0.39 inches) in length.
*Tooth—number.*—Four large between lobes.
*Tooth—shape.*—Convex.

Fruit:
*Ripe for commercial harvesting & shipment.*—Early August in the San Joaquin Valley of Central California.
*Solids.*—19.8.
*Acid.*—0.32.
*Sugar/acid ratio.*—61.8.
*Juice pH.*—4.05.
*Seeds.*—None.
*Capstem pedicel.*—12 mm (0.47 inches).
*Berry weight.*—11.36 grams.
*Juice color.*—P1.7 C7 Bonito Fuscous +.

Size:
*Cluster size.*—Large.
*Compactness.*—Compact.
*Cluster—weight.*—681.6 to 795.2 grams (1½ lbs. to 1¾ lbs.).
*Cluster—average length.*—24.5 cm (9.65 inches).
*Cluster—average width.*—15 cm (5.91 inches).
*Cluster—form.*—Conical.
*Stem variable.*—3.7–5.0 cm. (1.46–2.04 inches).
*Stem caliper.*—5 mm (0.197 inches).
*Berry—size.*—Large.
*Berry—shape.*—Ovate.
*Berry—number.*—60 to 70.
*Berry—average longitudinal.*—28 to 30 mm (1.10 to 1.18 inches).
*Berry—average transverse to longitudinal.*—23 to 25 mm. (0.91 to 0.98 inches).

Skin:
*Skin thickness.*—Medium.
*Texture.*—Firm.
*Blush color.*—Predominate color of berry P1.55 L8.
*Ground color.*—P1.14 K7 Byzantium.
*Pulp.*—Firm.
*Lenticels.*—0.

Flesh:
*Flesh color.*—Apical End — P1.46 16 Slate purple; stem end P1.20 K6 Piquant gr.
*Juice production.*—Very good.
*Flavor.*—Very good to excellent.
*Aroma.*—Mild.
*Texture.*—Firm.
*Ripening.*—Even.
*Eating quality.*—Very good to excellent.
*Use.*—Table grape.
*Keeping quality.*—Very good.
*Resistance to disease.*—Unknown.
*Harvesting and shipping.*—First week of August.
*Shipping and handling qualities.*—Very good.

Having thus described and illustrated our new variety of grapevine, we claim:

1. A new and distinct variety of grapevine as herein illustrated and described.

* * * * *

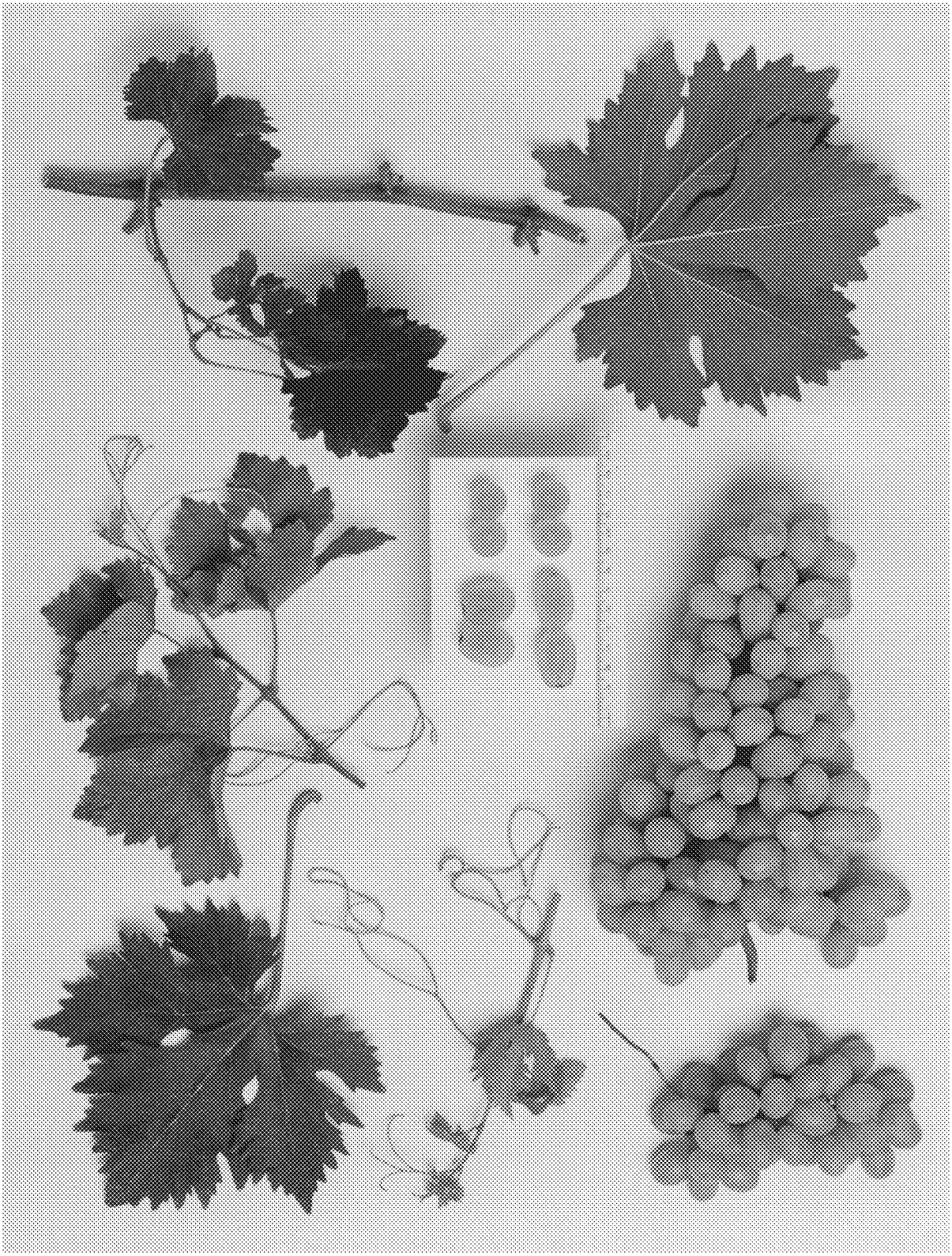

UNITED STATES PATENT AND TRADEMARK OFFICE

CERTIFICATE OF CORRECTION

PATENT NO. : PP21,316 P3
APPLICATION NO. : 11/594528
DATED : September 28, 2010
INVENTOR(S) : Timothy P. Sheehan It is certified that error appears in the above-identified patent and that said Letters Patent is hereby corrected as shown below:

Delete drawing sheet and substitute the drawing sheet as shown on the attached page.

Signed and Sealed this
Seventh Day of May, 2013

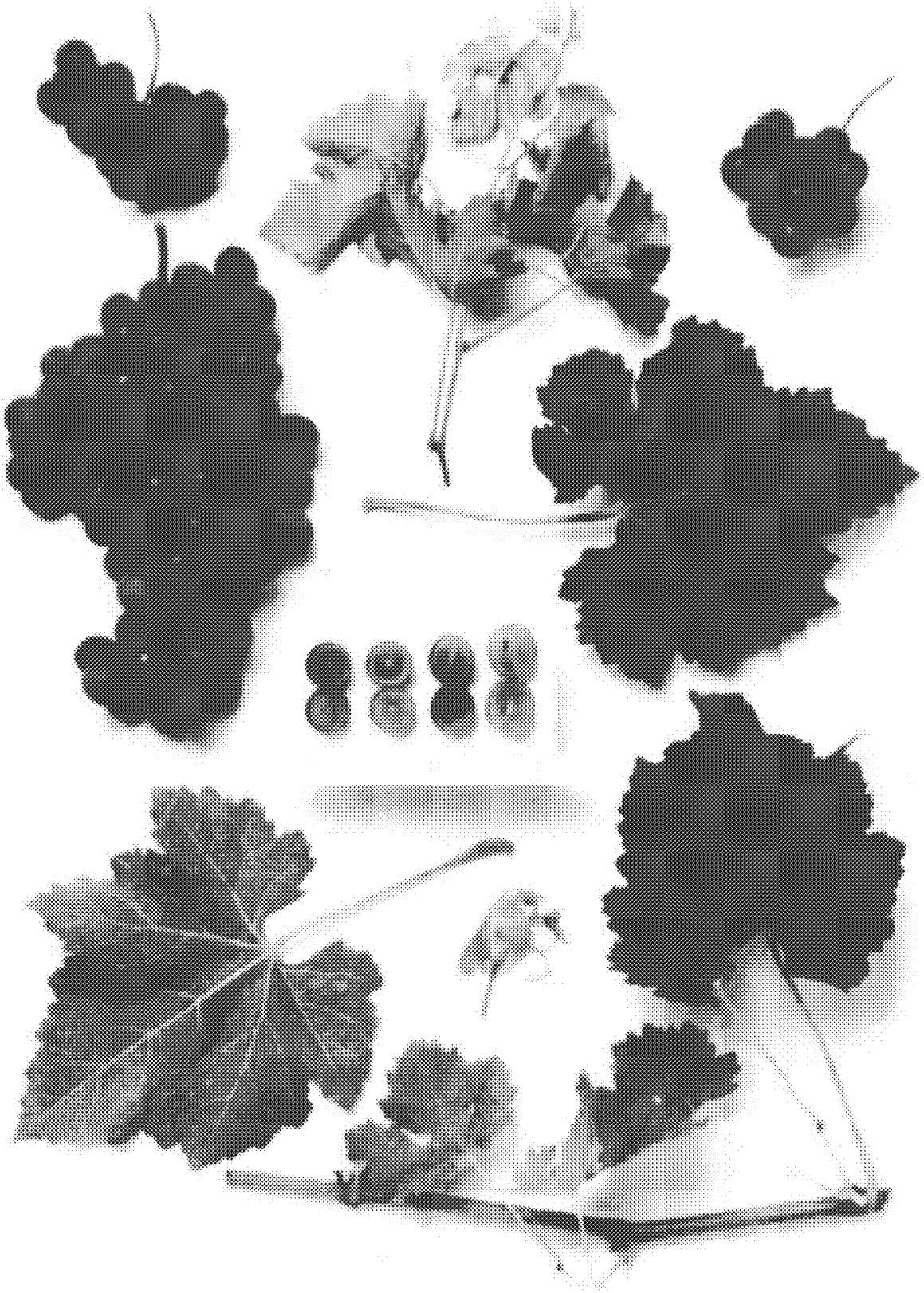

Teresa Stanek Rea
*Acting Director of the United States Patent and Trademark Office*